United States Patent
Stock et al.

(10) Patent No.: US 10,093,960 B2
(45) Date of Patent: Oct. 9, 2018

(54) LUMINESCENCE MEASUREMENT OF BIOLOGICAL SAMPLES UTILIZING DUAL REAGENTS

(71) Applicant: Molecular Devices, LLC, Sunnyvale, CA (US)

(72) Inventors: Daniel Stock, Hallein (AT); Georg Kronberger, Salzburg (AT); Michael Katzlinger, Eugendorf (AT)

(73) Assignee: Molecular Devices, LLC, San Jose, CA (US)

( * ) Notice: Subject to any disclaimer, the term of this patent is extended or adjusted under 35 U.S.C. 154(b) by 0 days.

(21) Appl. No.: 14/808,593

(22) Filed: Jul. 24, 2015

(65) Prior Publication Data
US 2017/0022537 A1     Jan. 26, 2017

(51) Int. Cl.
| | | |
|---|---|---|
| *C12Q 1/66* | (2006.01) | |
| *G01N 21/76* | (2006.01) | |
| *G01N 21/75* | (2006.01) | |

(52) U.S. Cl.
CPC ............... *C12Q 1/66* (2013.01); *G01N 21/76* (2013.01); *G01N 2021/754* (2013.01); *G01N 2201/12* (2013.01); *G01N 2333/90241* (2013.01)

(58) Field of Classification Search
CPC ..................... C12Q 1/66; G01N 21/76; G01N 2333/90241; G01N 2201/12
USPC ............................................................ 435/8
See application file for complete search history.

(56) References Cited

U.S. PATENT DOCUMENTS

| | | | |
|---|---|---|---|
| 5,082,628 A | * | 1/1992 | Andreotti ............... G01N 21/76 250/361 C |
| 6,891,618 B2 | | 5/2005 | Harju et al. |
| 8,119,066 B2 | | 2/2012 | Stock et al. |
| 8,227,205 B2 | * | 7/2012 | Niles ........................ C12Q 1/37 435/23 |
| 8,496,879 B2 | | 7/2013 | Atzler |
| 8,968,658 B2 | | 3/2015 | Katzlinger et al. |
| 2005/0012929 A1 | | 1/2005 | Booker et al. |
| 2005/0105080 A1 | | 5/2005 | Landlinger |
| 2011/0278472 A1 | | 11/2011 | Atzler |
| 2012/0077282 A1 | * | 3/2012 | Katzlinger ................ G01J 3/02 436/172 |
| 2013/0119277 A1 | | 5/2013 | Atzler et al. |
| 2014/0191138 A1 | | 7/2014 | Atzler et al. |

OTHER PUBLICATIONS

Promega Technical Manual TM040 (Aug. 2006), Dual-Luciferase Reporter Assay System.*
Promega Technical Manual TM278 (Mar. 2012), GloMax 96 Microplate Luminometer.*
Tellez et al. Characterization of Naturally-Occurring Humoral Immunity to AAV in Sheep. PLoS One (2013), v8(9), e75142, 11 pages.*

(Continued)

*Primary Examiner* — Sean C. Barron (57) ABSTRACT

In a method for measuring luminescence of a biological sample utilizing two different luminescence reagents, the sample is agitated to improve mixing with the second luminescence reagent, allowing for a shorter delay time between injection of the second reagent and measurement of the resulting luminescence activity. The improved mixing may also allow for a shorter measurement time, thereby improving throughput when assaying a large number of samples.

23 Claims, 4 Drawing Sheets

(56) References Cited

OTHER PUBLICATIONS

"Dual-Luciferase Reporter Assay and Dual-Luciferase Reporter 1000 Assay Systems", Instructions for use of products E1910, E1960 and E1980, Quick Protocol, 2003, 2009 Promega Corporation, www.promega.com.

"Dual-Luciferase Reporter Assay System", Instructions for use of Products E1910 and E1960, Technical Manual pp. 1-25, Promega Corporation, TM040 (6/11), www.promega.com.

\* cited by examiner

LUMINESCENCE MEASUREMENT OF BIOLOGICAL SAMPLES UTILIZING DUAL REAGENTS

TECHNICAL FIELD

This present invention generally relates to methods for measuring luminescence of a biological sample, particularly utilizing two different luminescence reagents such as firefly luciferase and *Renilla* luciferase substrates, and to components, apparatuses and systems utilized to perform such methods.

BACKGROUND

A useful modality for analyzing many types of samples is the measurement of luminescence (emission of light) by the sample. For example, in the case of a biological sample, luminescence is useful in the study of biochemical reactions, cellular physiology, gene expression, etc. Luminescence in a sample may result from the activity of a type of reporter enzyme known as luciferase, along with the injection of another reagent, coenzyme, and/or catalyst as needed for a particular application. Luminescence measurement may involve the use of a single type of luciferase. However, a so-called dual-reporter assay that entails the use of two different types of luciferase, such as firefly luciferase and *Renilla* luciferase, is often desired for its ability to minimize experimental variability and thereby improve the reliability of the data acquired. The second type of luciferase generates a subsequent signal while a quenching reagent suppresses or extinguishes the signal produced by the reaction with the first type of luciferase.

In an example of a dual-reporter assay protocol, the first type of luciferase is present in the pre-injection sample and the reagent generating the first signal is then added to the sample. After a delay period of typically a few seconds (e.g., two seconds), the resulting luminescent activity is measured over a period of time such as ten seconds. Then the reagent generating the second signal from the second type of luciferase is dispensed into the sample along with the quenching reagent. After a second delay period of again typically a few seconds, the resulting luminescent activity is measured over a period of time such as ten seconds. This dual-reporter assay protocol may be performed using a single-tube luminometer or a microplate (multi-well optical reader plate) luminometer.

A significant aspect of the dual-reporter assay is the mixing of the quenching reagent with the sample. The mixing needs to be effective enough, over the time period allotted by the protocol for mixing (after reagent injection and prior to measuring the activity of the second luciferase), to provide effective quenching of the signal produced by the first luciferase, and thereby to allow separation of the second signal from the first signal and thus acquire high-quality data. For example, the protocol may call for the first signal to be suppressed by 4 logs (more than 10,000 fold) before measuring the second signal. The afore-mentioned delay (mixing) period of about two seconds is often adequate for effective mixing when operating a single-tube or microplate luminometer with a conventional, relatively high reagent injection speed. A high injection speed, for example a flow rate on the order of hundreds of microliters per second ($\mu$L/sec), often imparts enough turbidity in the sample tube or well to result in effective mixing over a short period of time. However, for many microplate applications a lower injection speed would be desirable for reasons such as ensuring high dispensing accuracy, for example down to 1-$\mu$L increments. Due to the lower turbidity imparted by lower injection speeds, a short delay period may not provide sufficient time for effective mixing and consequently may not provide sufficient time for adequate quenching. Therefore, there is a need for providing a way to enhance or accelerate mixing in certain applications such as those utilizing low injection speeds and/or constrained to short mixing periods.

Moreover, when performing assays on a large number of samples using microplates, taking luminescence measurements on each sample over a long integration time such as ten seconds can require a large amount of total plate read time. Accelerating mixing may enable a reduction in the amount of time needed for taking luminescence measurements on each sample. Therefore, there is a need for providing a way to enhance or accelerate mixing in applications for which higher throughput is desired.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for measuring luminescence of a biological sample includes: dispensing a biological sample into a well; dispensing a first reagent into the well, wherein the sample reacts with the first reagent to emit a first luminescent light; after a first delay period, measuring the first luminescent light at a luminescence detector over a first measurement period; dispensing a second reagent into the well, wherein the sample reacts with the second reagent to emit a second luminescent light; after a second delay period, measuring the second luminescent light at the luminescence detector over a second measurement period; and agitating the well to enhance mixing of the second reagent with the sample, wherein agitating is initiated at a time selected from the group consisting of: while dispensing the second reagent; during the second delay period; and while measuring the second luminescent light.

In some embodiments, the first reagent and the second reagent are dispensed at a flow rate of 500 $\mu$L/sec or less, or in a range from 50 to 500 $\mu$L/sec, or 100 $\mu$L/sec or less, or in a range from 50 to 100 $\mu$L/sec, or at about 100 $\mu$L/sec.

According to another embodiment, a sample analyzing apparatus includes: a sample carrier configured for agitating a biological sample; a liquid dispensing system configured for dispensing selected reagents into contact with the sample; a luminescence detector configured for measuring luminescence light emitted from the sample; and a computing device configured for controlling the sample carrier, the liquid dispensing system and the liquid dispensing system to perform the any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not

DETAILED DESCRIPTION

Figure 1:
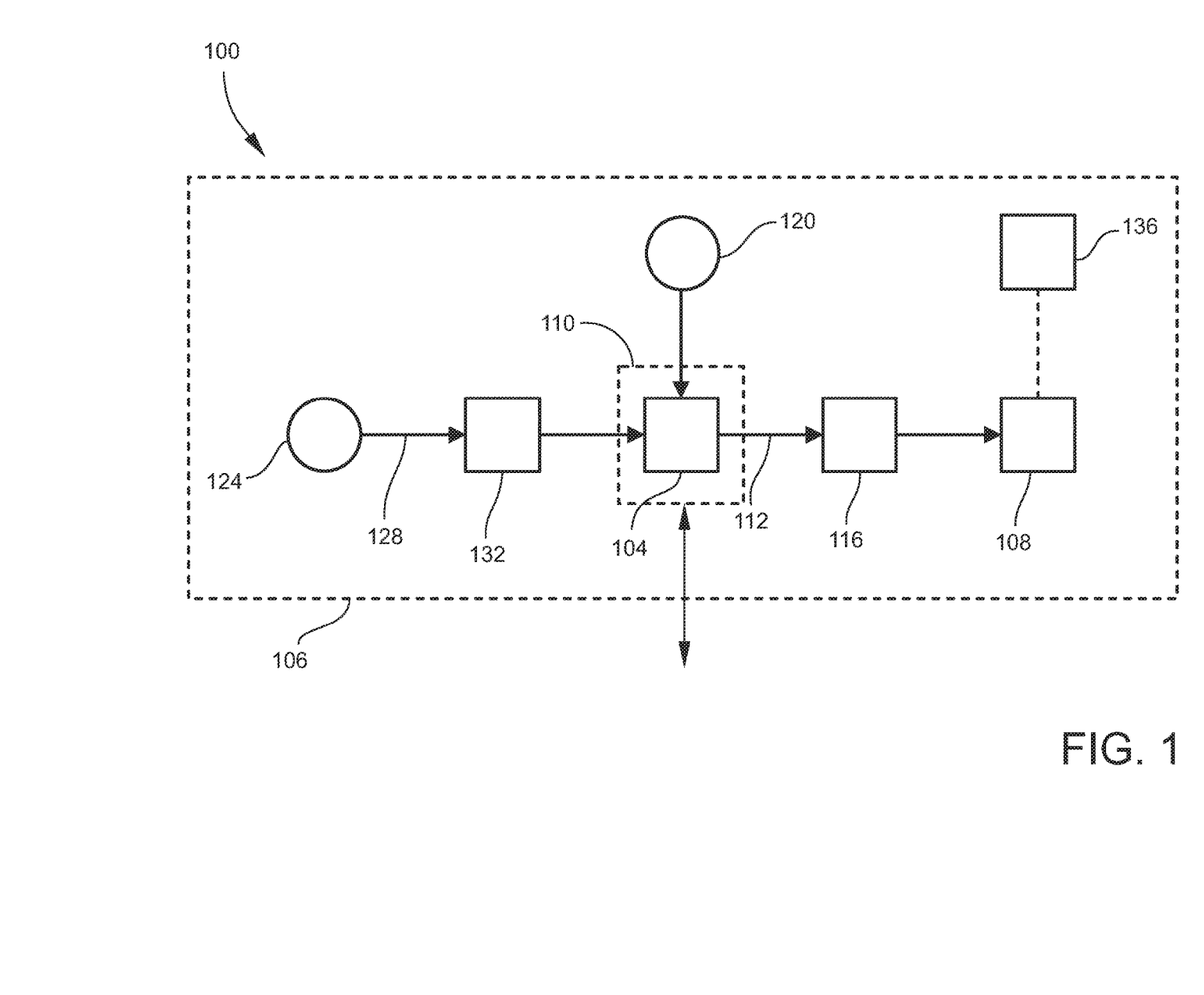
FIG. 1 is a schematic view of an example of a sample analyzing apparatus according to some embodiments.

FIG. 1 is a schematic view of an example of a sample analyzing apparatus or system 100 according to some embodiments. The sample analyzing apparatus 100 is configured for performing an optical measurement on a sample such as, for example, a chemical compound, a biological compound, a biological cell or component(s) thereof, etc. In specific embodiments disclosed herein, the optical measurement is based on luminescence. As used herein, the term "luminescence" may encompass chemiluminescence or bioluminescence.

In some embodiments, the sample analyzing apparatus 100 is configured as a dedicated luminometer. In other embodiments, however, the sample analyzing apparatus 100 may also be configured for performing optical measurements based on, for example, fluorescence, absorbance, spectroscopy, microscopy such as cell imaging, etc. For example, the sample analyzing apparatus 100 may be configured to enable a user to select a desired type of optical measurement to be performed. The user may be able to reconfigure the optics of the sample analyzing apparatus 100 to perform a desired type of luminescence, fluorescence, or absorbance measurement. Thus, in some embodiments the sample analyzing apparatus 100 may be a multi-mode reader. As appreciated by persons skilled in the art, a multi-mode reader is reconfigurable by enabling a user to select an application-specific cartridge among a number of different cartridges available, and load the selected cartridge into the multi-mode reader so as to establish optical and electrical circuits specific to the desired application. The selected cartridge is coupled to the instrument whereby the instrument is properly configured for carrying out the selected experiment. The cartridge may contain optics specific to or optimized for a particular type of application. The internal optics housed within the cartridge may communicate with external optics housed within the instrument through optical ports of the cartridge's housing. Some cartridges may additionally include an internal light source and/or light detector, depending on the type of optical measurement associated with such cartridges. Examples of cartridge-based multi-mode readers are described in U.S. Pat. Nos. 8,968,658; 8,496,879; 8,119,066; and 6,891,618; and in U.S. Patent Application Nos. 2014/0191138; (issued as U.S. Pat. No. 9,188,527); 2013/0119277; (issued as U.S. Pat. No. 9,347,882); 2011/0278472 (issued as U.S. Pat. No. 8,496,879); 2005/0105080; and 2005/0012929, the entire contents of each of which are incorporated by reference herein in their entireties.

Generally, the structure and operation of the various components provided in optical-based sample analysis instruments are understood by persons skilled in the art, and thus are only briefly described herein to facilitate an understanding of the presently disclosed subject matter. In the illustrated embodiment, the sample analyzing apparatus 100 includes a sample support 104 configured for supporting (or holding) one or more samples under analysis, and a light detector 108 configured for receiving and measuring emitted light 112 emitted from the sample. The sample support 104 when in an operative position for carrying out optical measurement of the sample, and the light detector 108 and other components illustrated in FIG. 1, may be enclosed in an apparatus housing 106 of the sample analyzing apparatus 100. The apparatus housing 106 may include one or more panels, doors, drawers, etc. for loading the sample support 104 and cartridges if provided, accessing interior regions and components of the sample analyzing apparatus 100, etc.

Generally, the sample support 104 may be one or more containers configured for holding one or more samples during an analysis. In embodiments typical for implementation of the subject matter disclosed herein, the sample support 104 is a multi-well plate (also known as a microtiter plate, microplate, or optical plate) containing a two-dimensional array of wells. The multi-well plate may have a standard format, such as 96-well or 384-well format, with a standard well size such as 100 microliters (µL). In other non-limiting examples, the sample support 104 may be one or more tubes, vials, cuvettes, etc., and may include a supporting frame or rack in which such containers are removably positioned. As used herein, the term "well" refers generally to any container that holds a single sample on which optical measurements are taken. Thus, several wells may be provided to contain distinct, individual samples on which respective optical measurements may be taken. Depending on the analysis being undertaken, the samples may be the same or different and/or may be measured under the same or different conditions. For example different reagents, or different quantities of reagents, may be added to different samples.

The sample support 104 may be disposed on a sample carrier (or sample support carrier) 110 configured for moving the sample support 104 along more or more axes. For example, the sample carrier 110 may be a manually actuated, or automated (e.g., motorized) stage or platform. The sample carrier 110 may be movable into and out from the apparatus housing 106, as indicated by an arrow in FIG. 1. A sample, or the sample support 104 containing one or more samples, may be mounted onto the sample carrier 110 while the sample carrier 110 is at an outside position, e.g., where the sample carrier 110 is positioned at least partially outside the apparatus housing 106. The sample carrier 110 may thus also be considered as a sample support. The sample carrier 110 may then be moved to an inside position at which the sample carrier 110 is positioned entirely in the apparatus housing 106 so as to align the sample (or sequentially align multiple samples) with an optical component and/or liquid handling component of the sample analyzing apparatus 100. In further embodiments, the sample carrier 110 is configured to agitate or shake the sample support 104 and thus agitate or shake the samples contained in the wells of the sample support 104. In some embodiments, the mode of agitation is orbital shaking whereby a swirling motion is imparted to the sample.

For luminescence detection, the light detector 108 is typically a photomultiplier tube (PMT). In other embodiments the light detector 108 may be of a different type such as, for example, a photodiode, a charge-coupled device (CCD), an active-pixel sensor (APS) such as a complementary metal-oxide-semiconductor (CMOS) device, etc., as needed to optimize sensitivity to the emission wavelengths to be detected. The optical input end of the light detector 108 typically includes a lens. The output end may include an electrical connector (e.g., contacts, terminals, pins, wire support, etc.) to provide power and enable measurement signals generated by the light detector 108 to be outputted to signal processing circuitry (e.g., data acquisition circuitry) provided with or external to the sample analyzing apparatus 100.

In typical embodiments, the sample analyzing apparatus 100 further includes emission optics 116 configured for transmitting the emitted light 112 from the sample to the light detector 108. The emission optics 116 may also be configured for processing the emitted light 112. Examples of processing include, but are not limited to, collecting, focusing, collimating, filtering, beam steering, beam splitting, and optical path switching. Thus, depending on the embodiment, the emission optics 116 may include one or more lenses, read heads, apertures, filters, light guides, mirrors, beam splitters, monochromators, diffraction gratings, prisms, optical path switches, etc. The emission optics 116 may be configured for receiving emitted light 112 from above the sample (e.g., a top read head) and/or below the sample (e.g., a bottom read head).

In typical embodiments, the sample analyzing apparatus 100 further includes a liquid dispensing system 120 (e.g., injector needle(s), tubing, pump(s), etc.) configured for adding a liquid to the sample (e.g., into selected wells of the sample support 104) before or after the sample has been operatively positioned in the sample analyzing apparatus 100. For example, a reagent may be added to the sample to induce luminescence, as appreciated by persons skilled in the art. The reagent may be, for example, a flash luminescence reagent (e.g., aequorin or other photoprotein) or a glow luminescence reagent (e.g., luciferase, luciferin). In some embodiments, two or more different types of reagents may be added. For example, firefly luciferase (*Photinis pyralis*) substrate may first be added followed by *Renilla* luciferase (*Renilla reniformis*, also known as sea pansy) substrate. In some embodiments, the second reagent may include a quenching agent that quenches the signal resulting from the previously added first reagent. As another example, labeling agents may be added for fluorescence or other types of measurements.

For embodiments in which the sample analyzing apparatus 100 is also capable for performing analyses requiring excitation of sample by photonic irradiation such as fluorescence measurements, the sample analyzing apparatus 100 includes one or more light sources 124 for producing excitation light 128 of a desired wavelength that is directed to the sample. Depending on the embodiment, the light source 124 may include a broadband light source (e.g., flash lamp) or one or more light emitting diodes (LEDs), laser diodes (LDs), etc. Multiple light sources 124 may be provided to enable a user to select a desired excitation wavelength. In typical embodiments, the sample analyzing apparatus 100 further includes excitation optics 132 configured for transmitting the excitation light 128 from the light source 124 to the sample. The excitation optics 132 may include, for example, one or more lenses, read heads, apertures, filters, light guides, mirrors, beam splitters, monochromators, diffraction gratings, prisms, optical path switches, etc., as noted above.

As also schematically illustrated in FIG. 1, the sample analyzing apparatus 100 may further include a computing device (or system controller) 136. As appreciated by persons skilled in the art, the computing device 136 may represent one or more modules configured for controlling, monitoring and/or timing various functional aspects of the sample analyzing apparatus 100. Thus, the computing device 136 may be configured for receiving data or other signals from the sample analyzing apparatus 100 such as measurement signals from the light detector 108, and/or for sending control signals to the light detector 108, the sample carrier 110, and the liquid dispensing system 120. In particular, the computing device 136 may control the actuation or movement of the sample carrier 110 for purposes such as moving (adjusting the position of) the sample support 104 and agitating the sample support 104, and may also control the operation of the liquid dispensing system 120 for purposes such as selecting a reagent to be dispensed (injected) into a well or other sample container, controlling the timing of dispensing (injecting) the reagent into the well and volume dispensed, controlling the flow rate (injection speed), etc. For all such purposes, the computing device 136 may communicate with various components of the sample analyzing apparatus 100 via wired or wireless communication links, as depicted by a dashed line between the computing device 136 and the light detector 108. For simplicity, other communication links that may be present between the computing device 136 and other components of the sample analyzing apparatus 100 are not shown. In typical embodiments, the computing device 136 includes a main electronic processor providing overall control, and may include one or more electronic processors configured for dedicated control operations or specific signal processing tasks. The computing device 136 may also include one or more memories and/or databases for storing data and/or software. The computing device 136 may also include a computer-readable medium 136 that includes instructions for performing any of the methods disclosed herein. The functional modules of the computing device 136 may comprise circuitry or other types of hardware (or firmware), software, or both. For example, the modules may include signal processing (or data acquisition) circuitry for receiving measurement signals from the light detector 108 and software for processing the measurement signals such as for generating graphical data. The computing device 136 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The computing device 136 may include an operating system (e.g., Microsoft Windows® software) for controlling and managing various functions of the computing device 136.

An example of a general method for analyzing a sample will now be described. The sample is introduced into the sample analyzing apparatus 100 and placed in a proper operating position relative to optics, fluidics, and other components of the sample analyzing apparatus 100 as appropriate. Generally, the "operating" position of the sample is an "optically aligned" position, i.e., a position that establishes an optical path sufficient for optical data acquisition from the sample. Depending on the experiment, the operating position may also correspond to the sample being "fluidly aligned" with the sample analyzing apparatus 100, i.e., positioned so as to be able to dispense fluid onto the sample such as by operating the liquid dispensing system 120. Sample introduction may entail loading or dispensing one or more samples into one or more wells of a microplate or other type of sample support 104, and loading or mounting the sample support 104 in the sample analyzing apparatus 100, such as with the use of a sample carrier 110 as noted above. Depending on the sample and the type of measurement to be made, the sample may be subjected to preparation or treatment (incubation, mixing, homogenization, centrifuging, buffering, reagent addition, etc.) prior to being positioned in the sample analyzing apparatus 100, as appreciated by persons skilled in the art.

In addition to sample introduction, depending on design the sample analyzing apparatus 100 or certain components thereof (optics, electronics, etc.) may need to be configured for implementing the specific type of measurement to be made. For example, if cartridge-based, the appropriate cartridge may be installed in the sample analyzing apparatus 100. After installing a cartridge, optics provided in the cartridge become part of the optical circuit within the housing 106 of the sample analyzing apparatus 100. For example, the cartridge optics may be aligned with (in optical communication with) the emission optics 116 and light detector 108, and in some embodiments also with the excitation optics 132 and light source 124. Installing the cartridge results in establishing electrical paths for transmitting power, data and control signals to and/or from the cartridge.

The sample is then processed as necessary to induce the emission of photons from the sample which, depending on the experiment (e.g., luminescence), may entail reagent addition using the liquid dispensing system 120 and/or irradiation/excitation (e.g., fluorescence, absorbance, etc.) using the light source 124 and associated excitation optics 132. The emission optics 116 collect the emitted light 112 from the sample and direct the emitted light 112 to the light detector 108. The light detector 108 converts these optical signals into electrical signals (detector signals, or "measurement" signals) and transmits the electrical signals to signal processing circuitry, such as may be provided by a computing device 136 of the sample analyzing apparatus 100 as described above. In the case of multiple samples, the sample support 104 may be moved (such as by using a sample carrier 110 as described above) to sequentially align each additional sample with the optics being utilized for the experiment, whereby measurements are taken from all samples sequentially.

Figure 2:
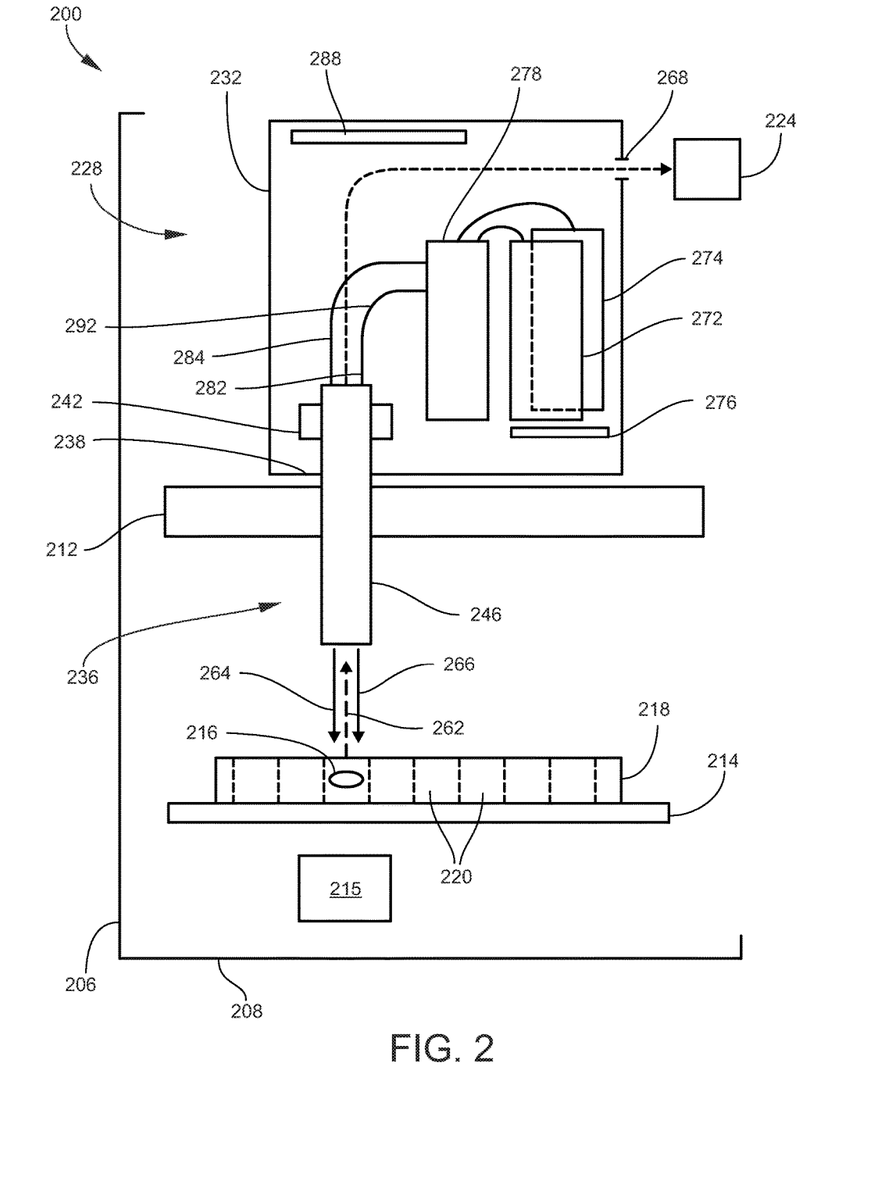
FIG. 2 is a schematic view of an example of a sample analyzing system or apparatus according to some embodiments.

FIG. 2 is a schematic view of another example of a sample analyzing system or apparatus 200 according to some embodiments. Generally, the structure and operation of any or all of the components of the sample analyzing apparatus 200 may be consistent with those described in conjunction with other embodiments disclosed herein. In the embodiment specifically illustrated in FIG. 2, the sample analyzing apparatus 200 is a multi-mode reader.

The sample analyzing apparatus 200 may generally include an apparatus housing enclosing various components of the sample analyzing apparatus 200. FIG. 2 illustrates a front wall 206 (or portion thereof) and a bottom wall 208 (or portion thereof) of the apparatus housing. The sample analyzing apparatus 200 may also generally include a movable cartridge support 212 configured for supporting one or more cartridges, and a movable sample carrier 214 for supporting one or more samples 216 under investigation or for supporting a sample support 218 that holds or contains such samples 216. As noted above, the sample support 218 is typically an optical plate providing a plurality of wells 220 containing individual samples 216. The cartridge support 212 may be movable between an inside cartridge support position (as illustrated) at which the cartridge support 212 is positioned entirely in the apparatus housing, and an outside cartridge support position at which the cartridge support 212 is positioned at least partially outside the apparatus housing to facilitate loading of one or more cartridges thereon. Similarly, the sample carrier 214 may be movable between an inside sample carrier position (as illustrated) at which the sample carrier 214 is positioned entirely in the apparatus housing, and an outside sample carrier position at which the sample carrier 214 is positioned at least partially outside the apparatus housing to facilitate loading of one or more samples 216 (or a sample support 218 holding one or more samples 216) thereon. As noted above, the sample carrier 214 may also be configured for agitating the samples 216 by mechanically agitating the sample support 218. The sample analyzing apparatus 200 may also generally include one or more optical detectors 224 configured for collecting optical detection signals from one or more different types of cartridges operatively loaded on the cartridge support 212.

FIG. 2 also illustrates an example of a luminescence cartridge 228 according to some embodiments. Like other cartridges that may be provided with the sample analyzing apparatus 200, the luminescence cartridge 228 is sized and configured to be removably loaded (i.e., mounted or installed) on the cartridge support 212, and may be replaced or exchanged with other cartridges of the same or different type as desired. The cartridge support 212 may be configured to support a plurality of cartridges simultaneously, and may be movable relative to internal components of the sample analyzing apparatus 200 so to enable a selected cartridge to be operably positioned for use in a selected type of sample analysis. The luminescence cartridge 228 includes a cartridge housing 232 and an injector assembly 236 at least partially disposed in the cartridge housing 232 and movable through an opening 238 of the cartridge housing 232. In typical embodiments, the injector assembly 236 is linearly movable in a reciprocating manner, i.e., the injector assembly 236 may be alternately extended and retracted. Hence, the injector assembly 236 is movable alternately toward and away from the cartridge housing 232, and thus alternately toward and away from the sample carrier 214 and any sample 216 with which the injector assembly 236 is operatively aligned. Depending on the design and location of the cartridge support 212, the cartridge support 212 may also include an opening to accommodate the movement of the injector assembly 236.

To actuate and control the movement of the injector assembly 236, the luminescence cartridge 228 includes a driver 242 (or drive mechanism, or drive assembly) that is coupled to the injector assembly 236. The driver 242 may be mounted at the cartridge housing 232 in any suitable manner, and in typical embodiments is contained within the interior of the cartridge housing 232. As appreciated by persons skilled in the art, the driver 242 may have any configuration suitable for moving (i.e., retracting and extending) the injector assembly 236 to any selected position relative to the cartridge housing 232 (and thus relative to the sample carrier 214 and any selected sample 216 supported thereon). In a typical embodiment, the driver 242 includes a motor (e.g., a micromotor) coupled to a linkage or transmission that is in turn coupled to the injector assembly 236. The driver 242 may include bearings or other appropriate components necessary for facilitating reliable and accurate actuation of the injector assembly 236. The linkage or transmission may have any configuration suitable for converting the rotational movement of the motor to linear movement of the injector assembly 236. For example, the linkage or transmission may include a set of gears such as a rack and pinion, a set of bevel gears, a worm and worm gear, etc.

To facilitate loading of luminescence cartridge 228 on the cartridge support 212 and subsequent removal therefrom, and to prevent damage to the injector assembly 236 during loading and removal, the injector assembly 236 may be fully retractable within the cartridge housing 232 by the driver 242 such that no part of the injector assembly 236 extends outside of the cartridge housing 232. The injector assembly 236 may also be moved to the fully retracted position while the cartridge support 212 is moving the injector assembly 236 (and any other cartridges loaded on the cartridge support 212) to different positions within the apparatus housing. However, the injector assembly 236 typically does not to be moved when acquiring luminescence data from multiple samples. That is, as noted elsewhere multiple samples may be provided at individual sites of a sample support 218, such as in different wells 220 of a multi-well plate that is supported on the sample carrier 214. The injector assembly 236 may be moved to a desired distance from the first sample 216 which, in the illustrated "top reading" example, is a desired elevation above the first sample 216. This desired distance will typically be the same for all samples contained on the sample support 218. Thus, the position of the injector assembly 236 typically does not need to be adjusted as the sample carrier 214 moves the sample support 218 to sequentially align one sample after another with the injector assembly 236 to take sequential luminescence readings.

In some embodiments, the sample analyzing apparatus 200 may also include a bottom read head 215, which may be appropriately coupled to optics and operate as generally described elsewhere in the present disclosure. The bottom read head 215 may be optically aligned with the injector assembly 236. This configuration enables injection from top and bottom fluorescence reading at the same time.

Figure 3:
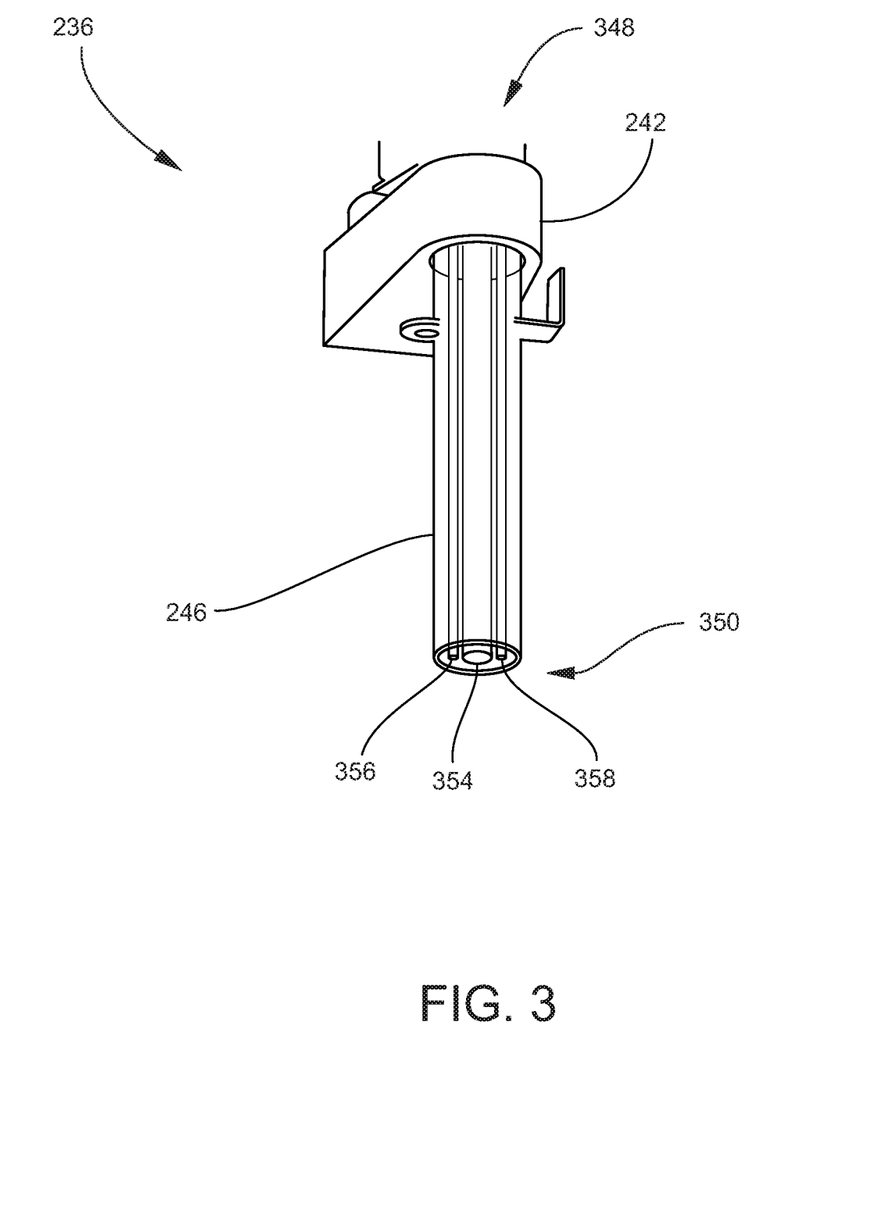
FIG. 3 is a perspective view of an example of an injector or injector/reader assembly according to some embodiments.

FIG. 3 is a perspective view of an example of the injector assembly 236 according to some embodiments. The injector assembly 236 includes an injector housing 246 generally elongated between a proximal end 348 and a distal end 350 of the housing 246. In typical embodiments, the injector housing 246 is cylindrical with a circular cross-section although in other embodiments may have a polygonal cross-section. The injector assembly 236 includes one or more injector needles 356 and 358 (two in the illustrated embodiment) extending through the injector housing 246 generally in parallel with each other. In some embodiments, the injector assembly 236 further includes a light guide 354 extending through the injector housing 246 generally in parallel with the injector needles 356 and 358. In such embodiments, the injector assembly 236 functions as a top reader as well as a liquid dispenser, and thus may also be referred to as an injector/reader assembly. The light guide 354 and the injector needles 356 and 358 may extend all the way down to the distal end 350 or may terminate at a small distance short of the distal end 350. The light guide 354 is configured for transmitting luminescent light emitted from the sample 216 (FIG. 2) to a luminescence detector, such as the optical detector 224 shown in FIG. 2. For this purpose, the light guide 354 may be an optical fiber, a light pipe, etc. The injector needles 356 and 358 are configured for dispensing fluid onto the sample 216 (e.g., into selected wells 220 of the sample support 218), such as reagents as may be utilized for glow luminescence or flash luminescence as appreciated by persons skilled in the art. The integration of the light guide 354 and the injector needles 356 and 358 into the single injector assembly 236 particularly facilitates flash luminescence. Moreover, the provision of two or more injector needles 356 and 358 facilitates the use of different types of reagents. For example, the first injector needle 356 may dispense a first reagent and the second injector needle 358 may dispense a second reagent, such as firefly luciferase substrate followed by *Renilla* luciferase substrate as described herein. Hence, the distal end 350 of the injector assembly 236 may serve both as an optical input and a fluid output of the injector assembly 236.

Referring back to FIG. 2, luminescent light directed into the injector assembly 236 from the sample 216 is depicted by a dashed arrow 262, and fluid streams directed out from the injector assembly 236 from the first injector needle 356 and second injector needle 358 (FIG. 3) are depicted by solid arrows 264 and 266, respectively. As also shown in FIG. 2, the cartridge housing 232 may include an optical port 268 aligned with the luminescence detector 224 for enabling the luminescent light to be transmitted to the luminescence detector 224. The dashed line leading from the injector assembly 236 to the luminescence detector 224 may represent light guide 354 (FIG. 3) extending out from the proximal end of the injector assembly 236 and to or through the optical port 268. Alternatively, the light guide 354 may terminate at some point in the cartridge housing 232, in which case the dashed line between the injector assembly 236 and the luminescence detector 224 may at least partially represent one or more other types of optical components (optical fiber, mirrors, etc.) configured for directing the luminescent light to the luminescence detector 224. As an alternative to utilizing the external luminescence detector 224, the luminescence cartridge 228 may include an internal detector (not shown) in the cartridge housing 232 that communicates with electronics of the sample analyzing apparatus 200 outside the luminescence cartridge 228.

As further shown in FIG. 2, the luminescence cartridge 228 includes one or more liquid reservoirs (e.g., bottles) such as reagent reservoirs 272 and 274. The reagent reservoirs 272 and 274 may be disposed on a reservoir support 276, which may be movable alternately into and out from the cartridge housing 232 for facilitating operations such as refilling the reagent reservoirs 272 and 274, rinsing or priming the liquid dispensing system, etc. The reagent reservoirs 272 and 274 may fluidly communicate with the injector assembly 236 via a pump 278 (e.g., a pump assembly or pump system). The pump 278 may represent one or more pumps (or pump units). For example, the first reagent reservoir 272 may communicate with the first injector needle 356 (FIG. 3) via a first fluid line 282 (e.g., tube) and a first pump to supply a first reagent, and the second reagent reservoir 274 may communicate with the second injector needle 358 (FIG. 3) via a second fluid line 284 and a second pump to supply a second reagent. The fluid lines 282 and 284, as well as the light guide 354, should have a length and flexibility sufficient to accommodate the alternating extension and retraction of the injector assembly 236.

Referring to FIG. 3, in some embodiments the injector assembly 236 does not include the light guide 354. In such embodiments luminescent light emitted from the sample 216 may, for example, be transmitted to the bottom read head 215 positioned below the sample 216 (i.e., below the sample carrier 214 and sample support 218 shown in FIG. 2) and routed via appropriate optics (e.g., a light guide such as an optical fiber) to the luminescence detector 224. Alternatively, luminescent light may transmitted directly to a luminescence detector (not shown) positioned below the sample 216, without utilizing a bottom read head 215 or other transmitting optics.

The luminescence cartridge 228 may also include electronics (circuitry) 288 configured for communicating with and/or controlling various components of the luminescence cartridge 228. The electronics 288 may include one or more circuits and other electrical hardware mounted on one or more support substrates such as, for example, printed circuit boards (PCBs). In addition to or as part of the electronics 288, the luminescence cartridge 228 may include an electrical connector configured for removable coupling to the sample analyzing apparatus 200 (e.g., a complementary electrical connector of sample analyzing apparatus 200) to receive power from and transmit signals to or from the sample analyzing apparatus 200. The electrical coupling may be implemented by plugs and sockets, male and female connectors, etc., whereby certain components of the luminescence cartridge 228 are placed in signal communication with a power source or system controller of the sample analyzing apparatus 200 as appropriate (e.g., the computing device 136 described above and illustrated in FIG. 1). In some embodiments, the electronics 288 (if provided) may be configured to directly control the operation of one or more of the components of the sample analyzing apparatus 200, or to coordinate with the computing device 136 (FIG. 1) described above in implementing such control, instead of such operation being solely controlled by the computing device 136 (FIG. 1) described above. For convenience, the term "computing device" encompasses both the computing device 136 shown in FIG. 1 and the electronics 288 shown in FIG. 2, unless specified otherwise or the context dictates otherwise.

An example of a general method for analyzing a sample 216 using the sample analyzing apparatus 200 will now be described with reference to FIGS. 2 and 3. The luminescence cartridge 228 is loaded (or installed) on the cartridge support 212 to position the luminescence cartridge 228 in the apparatus housing of the sample analyzing apparatus 200. Loading may include opening a panel or door such as may be located at the front wall 206 of the apparatus housing to access the cartridge support 212. The cartridge support 212 may first be moved to a position at least partially outside the apparatus housing, and after the luminescence cartridge 228 is loaded on the cartridge support 212, the cartridge support 212 may then be moved back into the apparatus housing with the luminescence cartridge 228 loaded thereon. Loading may also entail coupling the luminescence cartridge 228 with the sample analyzing apparatus 200 via electrical connectors as described above to establish paths for transmitting power, data and control signals. Before or after loading the luminescence cartridge 228, the sample 216 is loaded on the sample carrier 214, typically by first loading the sample 216 on a sample support 218 and in turn loading the sample support 218 on the sample carrier 214. A plurality of samples 216 may be loaded together on an appropriate sample support 218 such as a multi-well plate. Ultimately, the cartridge support 212 and the sample support 218 will be positioned relative to each other such that the sample 216 will be aligned with the injector assembly 236. In the present context, "aligned" means optically aligned, i.e., positioned so as to establish an optical path sufficient for luminescence data acquisition from the sample 216. The term "aligned" may also mean fluidly aligned, i.e., positioned so as to be able to dispense fluid onto the sample 216.

The injector assembly 236 is then moved toward the target sample 216 (the sample to be interrogated) until its optical input end reaches a desired distance (reading position) from the sample 216. The injector assembly 236 may be moved very close to the sample 216, thus maximizing light collection from the sample 216 and minimizing stray light collection from adjacent samples. At the reading position, the pump 278 is operated to establish a flow of a selected reagent from one of the reagent reservoirs 272 or 274 to the corresponding injector needle 356 or 358 (FIG. 3), whereby the selected reagent is injected by the injector needle 356 or 358 to the sample 216 to induce luminescence in the sample 216. The light guide 354 (FIG. 3) of the injector assembly 236 receives (collects) the resulting luminescent light 262 emitted from the sample 216 and transmits the luminescent light 262 to the luminescence detector 224 (or alternatively to an internal detector provided in the cartridge housing 232, not shown). The luminescence detector 224 converts these optical signals into electrical signals (detector signals, or measurement signals) and transmits the electrical signals to signal processing circuitry, such as may be provided by a system controller of sample analyzing apparatus 200, such as the computing device 136 described above and illustrated in FIG. 1. In the case of multiple samples 216, the sample carrier 214 may be moved to sequentially align each additional sample 216 with the light guide 354, whereby luminescence measurements are taken from all samples 216 sequentially. In some embodiments, the sample carrier 214 may quickly (e.g., in less than one second) translate the sample support 218 a small distance between dispensing the reagent and receiving the luminescent light 262, so as to center the injector needle 356 or 358 over the well 220 while dispensing the reagent and subsequently center the light guide 354 over the well 220 while receiving the luminescent light 262.

As described herein, in some embodiments more than one reagent may be utilized for each sample 216, such as when conducting a dual-reporter assay as appreciated by persons skilled in the art. For example, the pump 278 may establish a flow of a first reagent from the first reagent reservoir 272 to the first injector needle 356 (FIG. 3), after which the light guide 354 (FIG. 3) receives the (first) luminescent light 262 emitted from the sample 216 in response to injecting the first reagent. Subsequently, the pump 278 may establish a flow of a second reagent from the second reagent reservoir 274 to the second injector needle 358 (FIG. 3), after which the light guide 354 receives the (second) luminescent light 262 emitted from the sample 216 in response to injecting the second reagent. In some embodiments, the second reagent may include a quenching reagent that quenches the signal resulting from the first reagent, i.e., the second reagent may be a mixture of a second luminescence reagent and a quenching reagent effective for quenching the first luminescence reagent. As one non-limiting example, the first reagent may be Luciferase Assay Reagent II (LAR II) which includes firefly luciferase substrate, and the second reagent may be STOP & GLO® Reagent which includes *Renilla* luciferase substrate and a quenching reagent, both of which Reagents are provided in the DUAL-LUCIFERASE® Reporter (DLR™) Assay System commercially available from Promega Corporation, Madison, Wis., USA.

At the completion of making the luminescence measurements, the luminescence cartridge 232, being a modular or removable cartridge as described herein, may then be removed from the cartridge support 212, and thereafter replaced with another luminescence cartridge 232 or different type of removable cartridge as desired. Before moving the cartridge support 212 through the apparatus housing as needed to remove the luminescence cartridge 232, the injector assembly 236 may be retracted to a position completely inside the cartridge housing 232 to protect the injector assembly 236 during movement.

After the luminescence measurements have been completed, the injector system of the sample analyzing apparatus 200 (i.e., the pump 278, injector needles 356 and 358, and associated fluid lines, and also the reservoirs 272 and 274 if they are to subsequently contain a different type of liquid) may be rinsed and possibly decontaminated as needed to clean the injector system between experiments as well as to prevent the clogging of fluidic components such as the pump 278 and fluid lines. A suitable rinsing liquid may be pumped through the injector system for this purpose. In addition, as part of preparing the injector system for use before initiating the luminescence measurements, the injector system may need to be primed by pumping a small amount of each reagent through the respective fluid lines of the injector system.

In some embodiments, to initiate a rinse and/or priming operation, the cartridge support 212 is operated to move the luminescence cartridge 228 to an outside position relative to the apparatus housing. Once the cartridge support 212 and luminescence cartridge 228 are at the outside position, the reservoir support 276 and the reagent reservoirs 272 and 274 supported thereon may be moved to an outside position relative to the luminescence cartridge 228, by sliding the reservoir support 276. For this purpose, the reservoir support 276 may be movably mounted to the cartridge housing 232 by linear guides or tracks, etc., as appreciated by persons skilled in the art. At the outside position, the reagent reservoirs 272 and 274 may be replaced as needed. Additionally, after the cartridge support 212 and luminescence cartridge 228 have been moved to the outside position, an external rinsing/priming station (not shown) may be mounted to the cartridge support 212 and/or luminescence cartridge 228. The rinsing/priming station may include an external liquid container (or tank). In some embodiments, the rinsing/priming station may also include an external reservoir support for holding one or more rinsing/priming reservoirs (e.g., bottles). The external liquid container may include a port that is aligned with the injector assembly 236 when in the mounting position. Thus, after mounting the rinsing/priming station, the injector assembly 236 may be lowered into or through the port such that the injector assembly 236 fluidly communicates with the interior of the external liquid container. By this configuration, excess liquid flowed through the injector system during rinsing or priming is collected in the external liquid container. Examples of rinsing and priming operations carried out externally to the apparatus housing are described in U.S. patent application Ser. No. 14/566,708, filed on Feb. 3, 2015, titled LIQUID AND PLATE SENSORS FOR MICROPLATE INJECTOR SYSTEM, published as U.S. Patent Application No. 2016/0169808, the entire content of which is incorporated by reference herein.

According to other embodiments, the sample analyzing apparatus 200 shown in FIG. 2, or the sample analyzing apparatus 100 shown in FIG. 1, is an optical reader system that does not utilize cartridges, i.e., the sample analyzing apparatus is a non-cartridge based sample analyzing apparatus. The configuration of such a sample analyzing apparatus may be dedicated for luminescence-based measurement techniques. Alternatively, the sample analyzing apparatus may be reconfigurable for implementing different types of measurement techniques (e.g., luminescence, absorbance, fluorescence, etc.). For luminescence measurement entailing the use of a liquid injector system such as described above, one or more components of the liquid injector system may be removably mounted in the apparatus housing of the sample analyzing apparatus. For this purpose, a user may access the interior of the apparatus housing via a top panel (lid) or other panel or door of the apparatus housing. In such embodiments, instead of providing a cartridge support, the sample analyzing apparatus may include mounting features in the apparatus housing for mounting components of the injector system, including an injector assembly (such as the injector assembly 236 shown in FIG. 2, which may be configured as described above, with or without an integral light guide), one or more pumps, liquid lines, and reagent reservoirs. Generally, the structure and operation of any or all of the foregoing components of the sample analyzing apparatus may be consistent with those described above in conjunction with other embodiments disclosed herein. For example, FIGS. 1 and/or 2 may be considered as generally representative of such a sample analyzing apparatus, with the understanding various components would be positioned directly in the apparatus housing instead of in a cartridge. In such embodiments, the injector assembly may be mounted in a fixed position and the sample carrier may be moved to properly position the sample relative to the injector assembly. Thus, a driver for moving the injector assembly as described above need not be provided. In embodiments where the injector assembly does not include a light guide, a bottom read head as described above may be utilized.

In embodiments of the non-cartridge based sample analyzing apparatus, rinsing and priming may again be performed outside of the apparatus housing, by removing the injector assembly and other components of the injector system as needed to avoid dispensing liquid or liquid/air mixtures onto sensitive components in the interior of the apparatus housing. After the injector assembly has been moved to an outside position, an external rinsing/priming station including an external liquid container may be utilized in a manner analogous to the cartridge-based embodiments described above.

An example of a method for measuring luminescence of a biological sample utilizing two sequential luminescence reagents (i.e., a dual reporter assay) according to some embodiments will now be described. In some embodiments, the method may be implemented by operating the sample analyzing apparatus described above and illustrated in FIG. 1 or FIGS. 2 and 3. Moreover, the computing device (the computing device 136 shown in FIG. 1 and/or the electronics 288 shown in FIG. 2) may be configured for implementing one or more steps of the method through appropriate control of the components of the sample analyzing apparatus as described above.

According to the method, the sample is dispensed into a sample support such as a well. A first reagent is then dispensed (e.g., injected) into the well such that the first reagent contacts the sample. The period of time over which dispensing of the first reagent occurs may be referred to as a first reagent dispensing period (or first injection period). The sample reacts with the first reagent to emit a first luminescent light. After a first delay period, the first luminescent light is measured at a luminescence detector over a first measurement period. The first delay period may be considered as starting at the end of the first reagent dispensing period, and ending at the start of the first measurement period. Then, a second reagent is dispensed (e.g., injected) into the well, which occurs over a second reagent dispensing period (or second injection period). The sample reacts with the second reagent to emit a second luminescent light. As noted above, in a typical embodiment the second reagent includes a quenching reagent effective for quenching the reaction with the previously added first reagent. After a second delay period, the second luminescent light is measured at the luminescence detector over a second measurement period. The second delay period may be considered as starting at the end of the second reagent dispensing period, and ending at the start of the second measurement period.

In one specific yet non-limiting example of the present method, the sample may be a combination or mixture of one or more biological cells (or cell lysates) and a liquid such as a buffer solution. The first reagent may be or include firefly luciferase substrate. The volume of first reagent dispensed into the well may be about 100 µL. The second reagent may be or include *Renilla* luciferase substrate as well as a quenching reagent effective for quenching the firefly luciferase activity. The volume of first reagent dispensed into the well may be about 100 µL. It will be understood that other liquid volumes may be utilized, depending on such factors as well size, number of samples to be measured, throughput requirements, etc. Moreover, other reagents may be utilized depending on the particular experiment or assay being conducted. In some embodiments, the first delay period and the second delay period may be in a range from about 1 to 2 seconds. In some embodiments, the first measurement period and the second measurement period may be in a range from about 5 to 10 seconds.

According to an aspect of this method, the well containing the sample is agitated to enhance mixing (i.e., speed up the mixing process) of the second reagent with the sample. Such agitation may be initiated at one of the following points in time: while dispensing the second reagent; during the second delay period; or while measuring the second luminescent light. The point in time at which agitation is terminated may vary depending on the embodiment. Thus, if agitation is initiated while dispensing the second reagent, the agitation may be terminated before the start of the second delay period, or may be terminated during the second delay period, or may be continued through the second delay period and terminated while or after measuring the second luminescent light. If agitation is initiated during the second delay period, the agitation may be terminated before starting to measure the second luminescent light or after starting to measure the second luminescent light. Agitation by orbital shaking (or swirling) has been found to be particularly effective for enhancing the mixing of the second reagent and the sample, although other modes of agitation (e.g., side-to-side along one or two axes, rocking, etc.) may be suitable. As noted above, a platform or stage such as the sample carrier 110 shown in FIG. 1 or the sample carrier 214 shown in FIG. 3 may be configured and automated in a manner appreciated by persons skilled in the art to effect the mechanical agitation.

The above-described steps may be repeated on multiple samples, such as may be provided in a multi-well plate as described above. Thus, at the conclusion of the second measurement on one sample, the multi-well plate or the injector assembly (and read head, if applicable) may be moved so as to align the next well with the optics and fluidics, and the method then carried out on the next sample.

Agitation to enhance mixing may be beneficial in various applications. One example is an application in which high precision is required or desired when dispensing liquid volumes into sample wells, for example to allow the selection of accurate volumes in small increments (e.g., down to about 1 µL). One way to achieve high precision is to dispense a liquid in low-volume droplets, for example droplets having a volume as low as about 1 µL. Dispensing of low-volume droplets may be achieved by flowing the liquid to be dispensed at a low flow rate (low injection speed), utilizing a suitable low-flow rate pump (e.g., a peristaltic pump) and small-bore tubing, which may terminate at an injector needle as described herein. As a non-limiting example, in the context of the present disclosure a low flow rate is 500 µL/sec or less, or in a range from 50 to 500 µL/sec, or 100 µL/sec or less, or in a range from 50 to 100 µL/sec, with a more specific example being about 100 µL/sec. Dispensing at a low flow rate may also reduce the risk of bubble formation, spillage of liquid outside of the target well, and damage to adherent cell layers in the target well. However, as noted above in the background section of the present disclosure, the low flow rate induces less turbidity in the sample well, which may reduce the effectiveness of mixing in the well as compared to a more conventional, higher flow rate on the order of hundreds of µL/sec. The agitating action as disclosed herein is useful for promoting mixing and thereby counteracting any reduced mixing that might otherwise occur when dispensing at a low flow rate. The enhanced mixing resulting from agitation may be enable more effective suppression of the first luminescence signal over a shorter period of delay time (i.e., a shorter second delay period). Thus, according to some embodiments of the method for measuring luminescence of a biological sample, dispensing the first reagent and dispensing the second reagent are performed at a low flow rate as described above.

The enhanced mixing resulting from agitation may also enable a shorter second measurement period, which is particularly advantageous for improving throughput (total plate read time) when taking luminescence measurements on a large number of samples (using, for example, a multi-well plate). Thus, according to some embodiments of the method for measuring luminescence of a biological sample, the second delay period and/or second measurement period is less than about 2 seconds, or about 1 second. In further embodiments, the second delay period may be less than 1 second. The second delay period may even be reduced down to zero seconds (i.e., no delay) in applications where the second reagent dispensing period is sufficiently long to enable the second luminescence signal to reach an acceptable amplitude.

Figure 4:
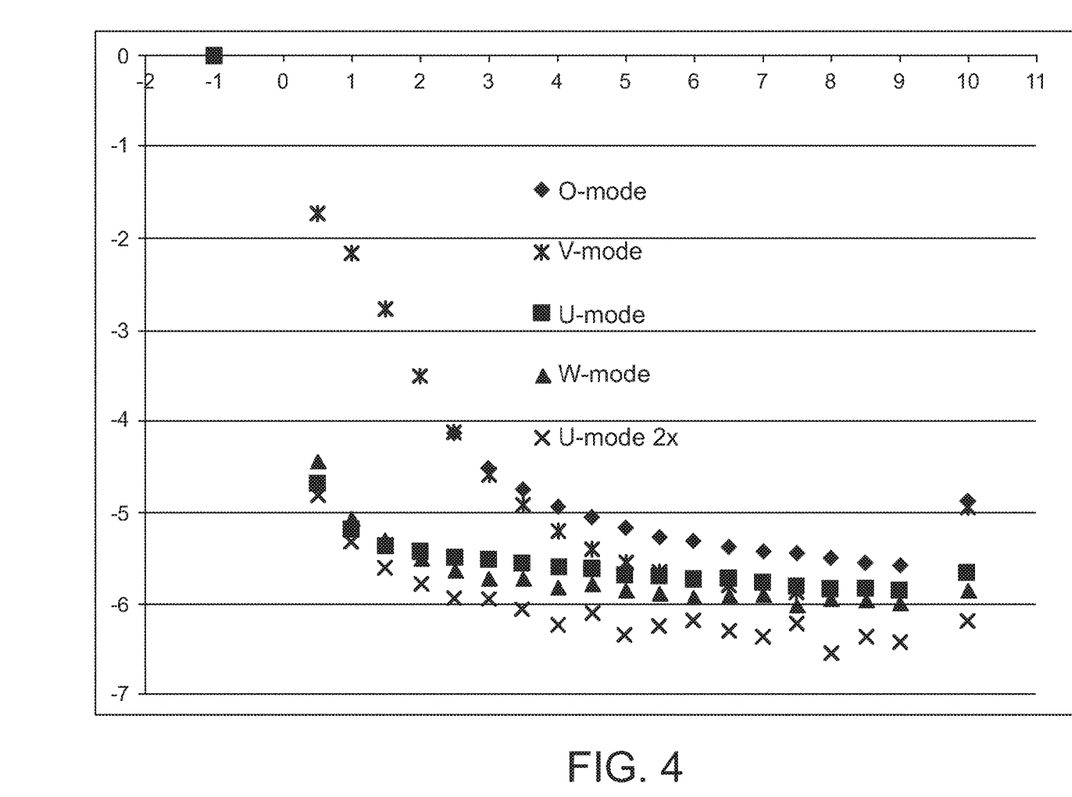
FIG. 4 is a graph plotting luminescence signals acquired during five experiments in which LAR II reagent is added to a sample, followed by adding STOP & GLO® Reagent to the sample, and agitating the sample according to some embodiments.

FIG. 4 is a graph plotting luminescence signals acquired during five experiments in which LAR II reagent is added to a sample, followed by adding STOP & GLO® Reagent to the sample, and agitating the sample in accordance with the dual luminescence method described herein. FIG. 4 plots the intensity of the first measurement signal on a log 10 scale, or $\log_{10}(x)$, as a function of time. In each experiment, the injection period for the second reagent is one second, starting at time t=−1 sec and ending at time t=0 sec, and the integration period over which data points are acquired is ten seconds, ending at time t=10 sec. Unless indicated otherwise, the protocol for each experiment was as follows: add 20 µL of firefly luciferase substrate (stock diluted 100-fold) to the sample; inject 100 µL of LAR II reagent; and inject 100 µL of STOP & GLO® Reagent. The flow rate (injection speed) was 100 µL/sec.

The five experiments shown in FIG. 4 are variations of the method described above, and are respectively labeled the O-mode, U-mode, V-mode, W-mode, and U-2x-mode. In the O-mode, the second delay period (time between second injection and measurement) is two seconds, and orbital shaking is performed over the second delay period. As shown in FIG. 4, reading begins at t=2, which is different than the other modes. In the U-mode, orbital shaking is performed during the second injection and is stopped while measuring the signal. In the V-mode, the second delay period is less than one second such that measurement is started almost immediately after the second injection. Orbital shaking is also started almost immediately after the second injection, and continues while the measurement is taken. It is seen that when shaking continues during the reading stage (V-mode) the data curve drops faster than would occur otherwise (O-mode), and hence the asymptotic effect of the quenching agent is achieved earlier in time. In the W-mode, orbital shaking is started during the second injection and continues while the measurement is taken. It is seen that when shaking is done during injection (U-mode and W-mode), the data curve drops faster, exceeding 5 logs at the first second after the injection is completed (t=0). In the U-2x-mode, the procedure is the same as the U-mode, but the STOP & GLO® Reagent is diluted twice and the volume injected is doubled. It is seen that all modes achieve 4 logs of suppression or greater. Moreover, the experiments shown in FIG. 4 demonstrate that shaking may enable the delay period to be reduced to one second or less (even down to zero), and further enable the measurement (or integration) period to be reduced down to one second. These reductions can result in significantly reduced total assay time when utilizing formats such as a 96-well microplate.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the computing device 136 schematically depicted in FIG. 1. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the computing device 136 in FIG. 1), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for measuring luminescence of a biological sample, the method comprising:
dispensing a biological sample into a well supported by a motorized sample carrier of a sample analyzing apparatus, the sample analyzing apparatus comprising a liquid dispensing system, the liquid dispensing system comprising a first injection needle, a second injection needle, a first reagent reservoir communicating with the first injection needle, and a second reagent reservoir communicating with the second injection needle;
aligning the first injection needle with the well by moving the sample carrier, moving the first injection needle, or moving both the sample carrier and the first injection needle;

dispensing a first reagent from the first injection needle into the well at a flow rate of 100 μL/sec or less by operating the liquid dispensing system, wherein the sample reacts with the first reagent to emit a first luminescent light;

after a first delay period, measuring the first luminescent light at a luminescence detector over a first measurement period;

dispensing a second reagent from the second injection needle into the well at a flow rate of 100 μL/sec or less by operating the liquid dispensing system while the well remains supported by the sample carrier, wherein the second reagent comprises a luminescent reagent effective for inducing emission of a second luminescent light, and a quenching reagent effective for suppressing emission of the first luminescent light, and wherein the sample reacts with the second reagent to emit the second luminescent light;

after a second delay period, measuring the second luminescent light at the luminescence detector over a second measurement period; and agitating the well to enhance mixing of the second reagent with the sample by operating the sample carrier to agitate the well in an automated manner, wherein:

the agitating is performed while the sample remains in the well and the well remains supported on the sample carrier; and the agitating is initiated at a time selected from the group consisting of: while dispensing the second reagent; during the second delay period; and while measuring the second luminescent light.

2. The method of claim 1, wherein the first delay period and the second delay period are each in a range from about 1 to 2 seconds.

3. The method of claim 1, wherein the first measurement period and the second measurement period are each in a range from about 5 to 10 seconds.

4. The method of claim 1, wherein at least one of the second delay period and the second measurement period is less than about 2 seconds, or less than about 1 second.

5. The method of claim 1, wherein the second measurement period is about 1 second.

6. The method of claim 1, wherein the first reagent comprises firefly luciferase substrate and the second reagent comprises *Renilla* luciferase substrate.

7. The method of claim 1, wherein agitating the well comprises shaking the well in an orbital manner.

8. The method of claim 1, wherein the well is one of a plurality of wells of a multi-well plate, and the method further comprises repeating the steps of claim 1 for one or more other samples respectively contained in one or more other wells of the multi-well plate.

9. The method of claim 1, wherein the first injector needle and the second injector needle are mounted in proximity to each other in an injector assembly, and further comprising, before dispensing the first reagent, positioning the injector assembly in alignment with the well.

10. The method of claim 9, wherein the injector assembly comprises a light guide communicating with the luminescence detector, and measuring the first luminescent light and the second luminescent light comprises transmitting the first luminescent light and the second luminescent light through the light guide.

11. The method of claim 9, wherein the well is a first well of a plurality of wells of a multi-well plate, and the method further comprises, after measuring the second luminescent light emitted from the sample in the first well, positioning the injector assembly in alignment with one or more other wells of the multi-well plate and, at each of the one or more other wells, repeating the steps of claim 1 for one or more other samples respectively contained in the one or more other wells.

12. The method of claim 1, wherein the first injector needle and the second injector needle are positioned in an injector housing of an injector assembly, and moving the first injector needle comprises moving the injector housing.

13. The method of claim 1, wherein the first injector needle and the second injector needle are mounted in a luminescence cartridge, and further comprising, before dispensing the first reagent, moving the luminescence cartridge into the sample analyzing apparatus.

14. The method of claim 13, wherein:

the first injector needle, the second injector needle, the first reagent reservoir, and the second reagent reservoir are disposed in the luminescence cartridge;

the luminescence cartridge comprises a pump unit fluidly coupling the first reagent reservoir with the first injector needle and fluidly coupling the second reagent reservoir with the second injector needle; and dispensing the first reagent and dispensing the second reagent comprise operating the pump.

15. The method of claim 13, comprising, before dispensing the first reagent, operating a driver of the luminescence cartridge to adjust a distance between the first injector needle and the well.

16. The method of claim 1, comprising, before or after dispensing the sample into the well, moving the sample carrier into an apparatus housing of the sample analyzing apparatus.

17. The method of claim 1, wherein agitating is initiated while dispensing the second reagent, and further comprising terminating the agitating at a time selected from the group consisting of: while dispensing the second reagent; during the second delay period; while measuring the second luminescent light; and after measuring the second luminescent light.

18. The method of claim 1, wherein agitating is initiated during the second delay period, and further comprising terminating the agitating at a time selected from the group consisting of: during the second delay period; while measuring the second luminescent light; and after measuring the second luminescent light.

19. The method of claim 1, wherein agitating is initiated while measuring the second luminescent light, and further comprising terminating the agitating at a time selected from the group consisting of: while measuring the second luminescent light; and after measuring the second luminescent light.

20. The method of claim 1, wherein aligning the first injection needle with the well comprises moving the sample carrier to center the first injection needle over the well, and further comprising, before dispensing the second reagent, moving the sample carrier to center the second injection needle over the well.

21. The method of claim 1, comprising operating a computing device to control respective operations of the sample carrier, the liquid dispensing system including the first injection needle and the second injection needle, and the luminescence detector, and to control timing of the respective operations, and to control durations of the respective operations.

22. The method of claim 1, wherein dispensing the first reagent comprises dispensing the first reagent in droplets from the first injection needle into the well, and dispensing the second reagent comprises dispensing the second reagent in droplets from the second injection needle into the well.

23. The method of claim 9, wherein aligning the first injection needle with the well comprises moving the sample carrier to center the first injection needle over the well, and further comprising:
- before measuring the first luminescent light, moving the sample carrier to center the light guide over the well;
- before dispensing the second reagent, moving the sample carrier to center the second injection needle over the well; and
- before measuring the second luminescent light, moving the sample carrier to center the light guide over the well.

* * * * *